United States Patent
Chibazakura et al.

(10) Patent No.: US 9,012,502 B2
(45) Date of Patent: Apr. 21, 2015

(54) CANCER HEAT THERAPY-ENHANCING AGENT

(75) Inventors: Taku Chibazakura, Tokyo (JP); Tohru Tanaka, Tokyo (JP); Kiwamu Takahashi, Tokyo (JP); Motowo Nakajima, Tokyo (JP); Fuminori Abe, Tokyo (JP)

(73) Assignees: SBI Pharmaceuticals Co., Ltd., Tokyo (JP); Tokyo University Agriculture Educational Corporation, Tokyo (JP)

( * ) Notice: Subject to any disclaimer, the term of this patent is extended or adjusted under 35 U.S.C. 154(b) by 125 days.

(21) Appl. No.: 13/820,303

(22) PCT Filed: Sep. 12, 2011

(86) PCT No.: PCT/JP2011/005119
§ 371 (c)(1),
(2), (4) Date: Mar. 1, 2013

(87) PCT Pub. No.: WO2012/035747
PCT Pub. Date: Mar. 22, 2012

(65) Prior Publication Data
US 2013/0158293 A1 Jun. 20, 2013

(30) Foreign Application Priority Data
Sep. 14, 2010 (JP) .................. 2010-206025

(51) Int. Cl.
A61K 31/221 (2006.01)
C07C 229/22 (2006.01)
A61K 31/197 (2006.01)

(52) U.S. Cl.
CPC ............. *C07C 229/22* (2013.01); *A61K 31/197* (2013.01)

(58) Field of Classification Search
CPC .......................... C07C 229/22; A61K 31/221
See application file for complete search history.

(56) References Cited

U.S. PATENT DOCUMENTS

2009/0324727 A1 * 12/2009 Foguet Roca ................. 424/489

FOREIGN PATENT DOCUMENTS

| CN | 101588792 A | 11/2009 |
| CN | 101588792 B | * 12/2009 |
| JP | 2006-056807 A | 3/2006 |
| WO | WO 2008/077641 A1 | 7/2008 |

OTHER PUBLICATIONS

Van der Zee, Annals of Oncology, Heating the Patient: A Promising Approach?, 2002, 13 pp. 1173-1184.*
Christensen et al, British Journal of Cancer, Effects of Haematoporphyrin Derivative and Light in Combination with Hyperthermia on Cells in Culture (1984), 50, pp. 85-89.*
Kelleher et al., "Enhanced effects of aminolaevulinic acid-based photodynamic therapy through local hyperthermia in rat tumours," British Journal of Cancer, 2003, 89:405-411.
Yanase et al., "Synergistic interaction of 5-aminolevulinic acid-based photodynamic therapy with simultaneous hyperthermia in an osteosarcoma tumor model," International Journal of Oncology, 2006, 29:365-373.
Frank et al., "Intensified oxidative and nitrosative stress following combined ALA-based photodynamic therapy and local hyperthermia in rat tumors," Int. J. Cancer, 2003, 107:941-948.

* cited by examiner

*Primary Examiner* — Paul A Zucker
(74) *Attorney, Agent, or Firm* — Foley & Lardner LLP

(57) ABSTRACT

Provided is an enhancer for cancer thermotherapy not combined with photodynamic therapy. Cancer treatment not combined with photodynamic therapy is made available by using, as an enhancer for cancer thermotherapy, 5-aminolevulinic acids represented by formula (1):

$$R^2R^1NCH_2COCH_2CH_2COR^3 \quad (1)$$

[wherein $R^1$ and $R^2$ each independently represent a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group] or a salt thereof.

5 Claims, 8 Drawing Sheets

CANCER HEAT THERAPY-ENHANCING AGENT

TECHNICAL FIELD

The present invention relates to an enhancer for cancer thermotherapy, and more particularly to an enhancer for cancer thermotherapy not combined with photodynamic therapy (PDT), comprising 5-aminolevulinic acids or a salt thereof.

BACKGROUND ART

Cancer (malignant tumor) is the most frequent cause of death in Japan, and one out of two Japanese is said to suffer from the disease. In addition, cancer is one of the leading causes of death among other developed countries. Accordingly, development of an effective treatment method for cancer has been a long-lasting goal of most people in the world including Japan. Cancer, however, derives from cells of a patient himself/herself. Thus, an effective therapeutic agent and/or method capable of effectively treating cancer without an adverse effect have not been easily developed, so that a potent therapeutic agent or method has yet to be reported.

Examples of current major cancer treatment include surgical treatment, chemotherapy, and radiotherapy. Recently, the treatment has extended to include thermotherapy and photodynamic therapy.

The above thermotherapy is a treatment method which takes advantage of the fact that cancer cells are heat-sensitive in nature compared to normal cells, and specifically inhibits proliferation of the cancer cells. That is, when a tissue containing cancer and normal cells is heated at about 42 to 43° C., homeostasis plays a role in the section of the normal cells to expand blood vessels surrounding the cells, thereby increasing their blood flow and dissipating heat. This allows the temperature of the cells to be kept at about 40° C., which results in almost no damage. In contrast, the section consisting of the cancer cells generally has insufficient blood flow, etc., and their homeostasis thus does not adequately function. As a result, the temperature of the cells rises to at or near the heating temperature, and the cells are killed at about 42.5° C. In this regard, however, when there is a large heating area in thermotherapy or when cancer to be treated is at some depth from the body surface, the patient's burden due to heating unfortunately increases.

The above-described photodynamic therapy is a treatment method including: administrating a photosensitizer or a precursor thereof having an affinity for a cancerous tissue to a patient; subsequently irradiating the cancerous tissue with a laser beam to excite the photosensitizer; and generating reactive oxygen to kill cancer cells. For example, Patent Document 1 discloses a photodynamic therapy formulation in which at least one drug, including a photosensitizing compound, is encapsulated inside a lipid membrane or in an internal aqueous phase thereof and in which a liposome substantially free of an organic solvent is included. Patent Document 1 also discloses that protoporphyrin IX (PpIX) is among preferable photosensitizing compounds, and that 5-aminolevulinic acid (5-ALA), which is a PpIX precursor, selectively induces PpIX production in tumors. In addition, Patent Document 1 describes a combination between photodynamic therapy and thermotherapy.

In view of the above, 5-ALA is a PpIX precursor which is a photosensitizer. Accordingly, when 5-ALA is used for cancer treatment, at least photodynamic therapy is implemented, and occasional use of a combination with additional thermotherapy has been previously known. So far, no cancer treatment applications using 5-ALA but not using the photodynamic therapy have been reported.

PRIOR ART DOCUMENTS

Patent Documents

Patent Document 1: Japanese unexamined Patent Application Publication No. 2006-56807

SUMMARY OF THE INVENTION

Object to be Solved by the Invention

It is an object of the present invention to provide an enhancer for cancer thermotherapy not combined with photodynamic therapy.

Means to Solve the Object

As described in Background Art, since 5-ALA is a PpIX precursor which is a photosensitizer, use of 5-ALA for cancer treatment involving at least photodynamic therapy, occasionally further combined with thermotherapy, has been previously known. The present inventors have conducted intensive research under such circumstances, and found that even when used in cancer thermotherapy not combined with photodynamic therapy, 5-ALA can enhance an anticancer effect while having a totally unclear mechanism of action. Then, the present inventors have completed the present invention.

Specifically, the present invention relates to [1] an enhancer for cancer thermotherapy not combined with photodynamic therapy, comprising 5-aminolevulinic acids represented by formula (1):

$$R^2R^1NCH_2COCH_2CH_2COR^3 \qquad (1)$$

[wherein $R^1$ and $R^2$ each independently represent a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group] or a salt thereof, and

[2] the enhancer for cancer thermotherapy according to the above [1], wherein the 5-aminolevulinic acids or a salt thereof are not encapsulated inside a lipid membrane or in an internal aqueous phase thereof.

In addition, other embodiments of the present invention include: cancer thermotherapy not combined with photodynamic therapy, wherein 5-aminolevulinic acids represented by formula (1) or a salt thereof are administered to a subject; use of 5-aminolevulinic acids represented by formula (1) or a salt thereof in the preparation of a medicament or a enhancer for cancer thermotherapy not combined with photodynamic therapy; and a therapeutic agent for cancer thermotherapy not combined with photodynamic therapy, comprising 5-aminolevulinic acids represented by formula (1) or a salt thereof.

Effect of the Invention

The present invention can markedly enhance an anticancer effect in cancer thermotherapy not combined with photodynamic therapy. In addition, according to the present invention, even if a level of heating is a little lower in thermotherapy, a sufficient anticancer effect can be achieved. Accordingly, when there is a large heating area in the thermotherapy or when cancer to be treated is at some depth from the body surface, the patient's burden due to heating can be reduced.

Further, cancer thermotherapy utilizing an enhancer for cancer thermotherapy according to the present invention has an advantage over photodynamic therapy. Examples of the advantage include having an anticancer effect on cancer at a location hard to irradiate with light. Moreover, the present invention can exert an excellent anticancer effect on cancer cells while minimizing damage to normal cells.

MODE OF CARRYING OUT THE INVENTION

Figure 1:
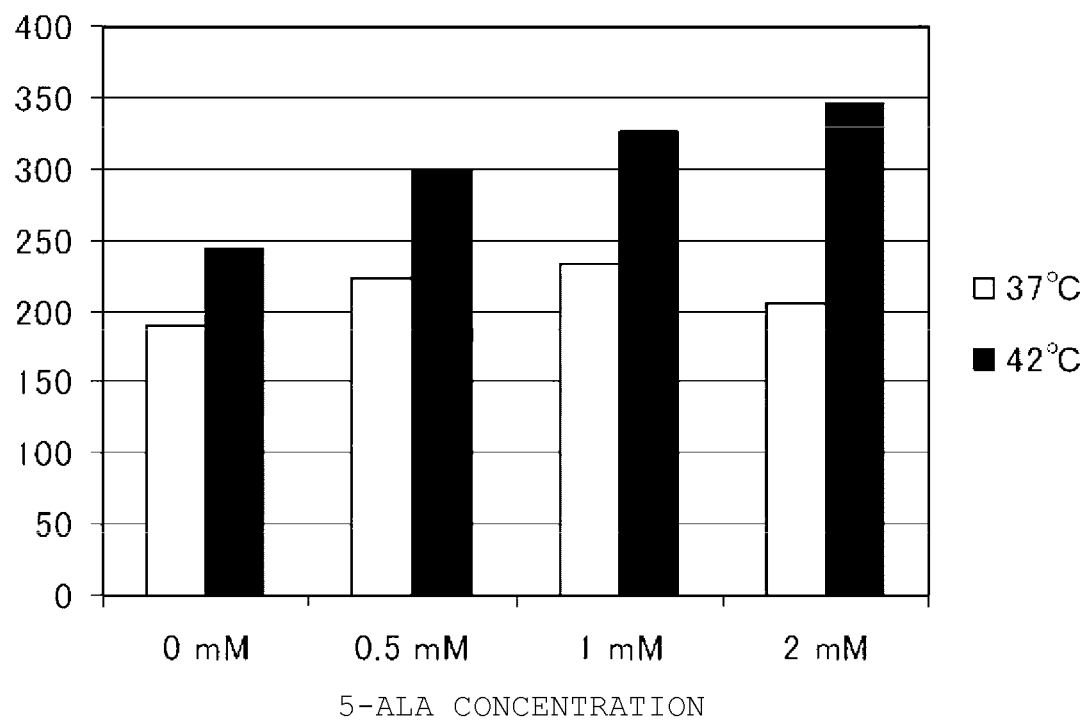
FIG. 1 illustrates the results of an assay for intracellular reactive oxygen species in a human embryonic kidney cell line HEK293. In the graph, the abscissa represents a 5-ALA concentration (mM), and the ordinate represents a fluorescence peak value derived from DCF-DA.

[Enhancer for Cancer Thermotherapy according to the Present Invention]

An enhancer for cancer thermotherapy according to the present invention (hereinafter, sometimes simply referred to as "an enhancer of the present invention") is an enhancer for cancer thermotherapy not combined with photodynamic therapy. There is no particular limitation as long as the enhancer of the present invention comprises 5-aminolevulinic acids (hereinafter, sometimes referred to as "5-aminolevulinic acids according to the present invention") represented by formula (1):

$$R^2R^1NCH_2COCH_2CH_2COR^3 \tag{1}$$

[wherein $R^1$ and $R^2$ each independently represent a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group] or a salt thereof. The "cancer thermotherapy effect" means an anticancer effect resulting from the cancer thermotherapy.

Note that human normal cells preferentially perform aerobic metabolism. Accordingly, 5-aminolevulinic acids administered can be metabolized to heme and cytochrome. In contrast, cancer cells preferentially perform anaerobic metabolism. Accordingly, the present inventors have found that 5-aminolevulinic acids administered accumulate in the cancer cells as a heme and cytochrome precursor, protoporphyrin IX (see Japanese Patent Application No. 2009-161657). The details on the mechanism of action of the present invention remain unclear. However, when cancer thermotherapy is performed under conditions in which an enhancer of the present invention causes a relatively large accumulation of protoporphyrin IX in cancer cells, a level of reactive oxygen species generated in the cancer cells markedly increases. This seems to markedly enhance an anticancer effect in the cancer thermotherapy (hereinafter, sometimes referred to as "an enhancing effect of the present invention"). As a result, an enhancer of the present invention can markedly enhance an anticancer effect in the cancer thermotherapy. In addition, even if a level of heating is a little lower in thermotherapy, a sufficient anticancer effect can be achieved. Accordingly, when there is a large heating area in the thermotherapy or when cancer to be treated is at some depth from the body surface, the patient's burden due to heating can be reduced.

In formula (1), $R^1$ and $R^2$ each independently represent a hydrogen atom, an alkyl group, an acyl group, an alkoxycarbonyl group, an aryl group, or an aralkyl group.

The above alkyl group is preferably a linear or branched alkyl group containing 1 to 24 carbon atoms, more preferably an alkyl group containing 1 to 18 carbon atoms, and particularly preferably an alkyl group containing 1 to 6 carbon atoms. Examples of the foregoing alkyl group containing 1 to 6 carbon atoms include a methyl group, an ethyl group, a n-propyl group, an isopropyl group, a n-butyl group, and a sec-butyl group.

The above acyl group is preferably a linear or branched alkanoyl, alkenylcarbonyl, or aroyl group containing 1 to 12 carbon atoms, and particularly preferably an alkanoyl group containing 1 to 6 carbon atoms. Examples of the foregoing acyl group include a formyl group, an acetyl group, a propionyl group, and a butyryl group.

The above alkoxycarbonyl group is preferably an alkoxycarbonyl group containing a total of 2 to 13 carbon atoms, and particularly preferably an alkoxycarbonyl group containing 2 to 7 carbon atoms. Examples of the foregoing alkoxycarbonyl group include a methoxycarbonyl group, an ethoxycarbonyl group, a n-propoxycarbonyl group, and an isopropoxycarbonyl group.

The above aryl group is preferably an aryl group containing 6 to 16 carbon atoms. Examples include a phenyl group and a naphthyl group.

The above aralkyl group is preferably a group consisting of an aryl group containing 6 to 16 carbon atoms and the above alkyl group containing 1 to 6 carbon atoms. Examples include a benzyl group.

In the above formula (1), $R^3$ represents a hydroxy group, an alkoxy group, an acyloxy group, an alkoxycarbonyloxy group, an aryloxy group, an aralkyloxy group, or an amino group.

The above alkoxy group is preferably a linear or branched alkoxy group containing 1 to 24 carbon atoms, more preferably an alkoxy group containing 1 to 16 carbon atoms, and particularly preferably an alkoxy group containing 1 to 12 carbon atoms. Examples of the foregoing alkoxy group include a methoxy group, an ethoxy group, a n-propoxy group, an isopropoxy group, a n-butoxy group, a pentyloxy group, a hexyloxy group, an octyloxy group, a decyloxy group, and a dodecyloxy group.

The above acyloxy group is preferably a linear or branched alkanoyloxy group containing 1 to 12 carbon atoms, and particularly preferably an alkanoyloxy group containing 1 to 6 carbon atoms. Examples of the foregoing acyloxy group include an acetoxy group, a propionyloxy group, and a butyryloxy group.

The above alkoxycarbonyloxy group is preferably an alkoxycarbonyloxy group containing a total of 2 to 13 carbon atoms, and particularly preferably an alkoxycarbonyloxy group containing a total of 2 to 7 carbon atoms. Examples of the foregoing alkoxycarbonyloxy group include a methoxycarbonyloxy group, an ethoxycarbonyloxy group, a n-propoxycarbonyloxy group, and an isopropoxycarbonyloxy group.

The above aryloxy group is preferably an aryloxy group containing 6 to 16 carbon atoms. Examples include a phenoxy group and a naphthyloxy group. The aralkyloxy group is preferably a group having the above aralkyl group. Examples include a benzyloxy group.

In formula (1), a hydrogen atom is preferred as $R^1$ and $R^2$. $R^3$ is preferably a hydroxy group, an alkoxy group, or an aralkyloxy group, more preferably a hydroxy group or an alkoxy group containing 1 to 12 carbon atoms, and particularly preferably a methoxy group or a hexyloxy group.

A compound represented by formula (1), wherein $R^1$ and $R^2$ each represent a hydrogen atom and $R^3$ is a hydroxy group, is 5-aminolevulinic acid, which is particularly preferred. Preferable examples of 5-aminolevulinic acids other than 5-aminolevulinic acid (i.e., 5-aminolevulinic acid derivatives) include 5-aminolevulinates (e.g., methyl-5-aminolevulinate, ethyl-5-aminolevulinate, propyl-5-aminolevulinate, butyl-5-aminolevulinate, pentyl-5-aminolevulinate, hexyl-5-aminolevulinate). Particularly preferred is methyl-5-aminolevulinate or hexyl-5-aminolevulinate. Japanese unexamined Patent Application Publication (Translation of PCT Application) No. 11-501914, for example, discloses that 5-aminolevulinate exhibits the same physiological effect as 5-aminolevulinic acid.

Salts of 5-aminolevulinic acids are preferably, but not particularly limited to, pharmaceutically acceptable acid addition salts of inorganic or organic acid. Examples of the inorganic acid addition salt include hydrochloride, hydrobromide, sulfate, nitrate, and phosphate. Examples of the organic acid addition salt include acetate, lactate, citrate, tartrate, succinate, maleate, fumarate, and ascorbate. Particularly preferred is 5-aminolevulinic acid hydrochloride or 5-aminolevulinic acid phosphate. These salts can be produced by any one of methods using a chemical synthesis, microorganism, or enzyme. Examples include methods described in Japanese unexamined Patent Application Publication No. 4-9360, Japanese unexamined Patent Application Publication (Translation of PCT Application) No. 11-501914, Japanese unexamined Patent Application Publication No. 2006-182753, Japanese unexamined Patent Application Publication No. 2005-314361, or Japanese unexamined Patent Application Publication No. 2005-314360.

An amount of the 5-aminolevulinic acids according to the present invention included in an enhancer of the present invention is not particularly limited as long as an enhancing effect of the present invention can be achieved. The amount may be, for example, 0.0001 to 99.9999% by mass per total amount of the enhancer of the present invention, preferably 0.001 to 80% by mass, more preferably 0.001 to 50% by mass, and still more preferably 0.005 to 20% by mass.

As long as an enhancing effect of the present invention is achieved, an enhancer of the present invention optionally contains, in addition to the 5-aminolevulinic acids according to the present invention, any component such as another substance which enhances an anticancer effect in cancer thermotherapy.

An appropriate formulation can be formulated according to a common procedure from the 5-aminolevulinic acids according to the present invention. A solid formulation such as powder medicines and granules may be employed as a dosage form of the formulation. In view of easy-to-use characteristics, however, preferred is a liquid formulation such as a solution, emulsion, and suspension. Suitable examples of a method for producing the above-described liquid formulation include a method for mixing 5-aminolevulinic acids according to the present invention and a solvent, and a method for mixing the resulting mixture with an additional suspending agent and/or emulsifier. As described above, when the 5-aminolevulinic acids according to the present invention is formulated, any components can be added depending on the pharmaceutical need. Examples of the components include suitable carriers such as excipients, bonding agents, solvents, solvent aids, suspending agents, emulsifiers, tonicity agents, buffers, stabilizers, soothing agents, preservatives, antioxidants, coloring agents, lubricants, disintegrants, moisturizers, adsorbents, sweetening agents, and diluents. A preferable enhancer of the present invention includes an agent in which 5-aminolevulinic acids according to the present invention are not encapsulated inside a lipid membrane or in an internal aqueous phase thereof.

An enhancer of the present invention can enhance an anticancer effect in cancer thermotherapy not combined with photodynamic therapy either in vitro or in vivo. But, preferred may be a method using the enhancer in vivo. For example, the method using the enhancer in vitro can include the steps of: (a) causing an enhancer of the present invention to contact with cells of interest; and (b) heating the cells of interest to a range from 41 to 44° C. (preferably 42 to 43° C.). Preferable examples of step (a) can include step (a1) of culturing cells of interest under conditions in contact with an enhancer of the present invention for a certain period (preferably 5 minutes to 25 hours, more preferably 10 minutes to 15 hours, still more preferably 3 to 7 hours, and still more preferably 5 hours). Preferable examples of step (b) can include step (b1) of heating the cells of interest to a range from 41 to 44° C. (preferably 42 to 43° C.) and keeping the cells of interest at a temperature within the range for 10 minutes to 5 hours (preferably 15 minutes to 3 hours, more preferably 20 minutes to 2 hours, and still more preferably 30 to 60 minutes).

An amount of the enhancer of the present invention used in vitro is not particularly limited as long as an enhancing effect of the present invention can be achieved. The concentration in a medium contacting the cells of interest may be, for example, 0.1 µM to 1000 mM, and preferably 10 µM to 50 mM of the 5-aminolevulinic acids.

For example, the method using an enhancer of the present invention in vivo can include the steps of: (A) administering an enhancer of the present invention to a subject; and (B) heating a cancer lesion of the subject to a range from 41 to 44° C. (preferably 42 to 43° C.) Preferable examples of step (A1) can include a step of administering an enhancer of the present invention to a subject and thereafter waiting for a certain period (preferably 5 minutes to 25 hours, more preferably 10 minutes to 15 hours, still more preferably 3 to 7 hours, and still more preferably 4 to 6 hours). Preferable examples of step (B) can include step (B1) of heating the cancer lesion of the subject to a range from 41 to 44° C. (preferably 42 to 43° C.) and keeping the lesion at a temperature within the range for 10 minutes to 5 hours (preferably 15 minutes to 3 hours, more preferably 20 minutes to 2 hours, and still more preferably 25 to 90 minutes, still more preferably 30 to 75 minutes, and still more preferably 40 to 60 minutes). Waiting for a certain period in step (A1) makes it possible to accumulate more protoporphyrin IX, a metabolite of 5-aminolevulinic acids included in an enhancer of the present invention, in cancer cells. This makes it possible to achieve a much better enhancing effect of the present invention.

Examples of the method for administering an enhancer of the present invention to a subject can include injections (e.g., intravenous, intramuscular, intra-arterial administration); oral administration; transdermal administration; transmucosal administration; transrectal administration; transluminal administration; and topical administration into the brain or the like. Among them, preferred are intravenous, intramuscular, and intra-arterial injections; oral administration; and transdermal administration.

An in vivo dosage of an enhancer of the present invention is not particularly limited as long as an enhancing effect of the present invention can be achieved. The dosage, however, may be preferably 1 to 10000 mg per adult a day of the 5-aminolevulinic acids according to the present invention, more preferably 3 to 3000 mg, and still more preferably 10 to 1000 mg. What time an enhancer of the present invention is administered is not particularly limited. Either morning or evening is allowed. When there is a high dosage, however, the dosage may be divided into multiple doses.

The in vitro or in vivo heating procedure is not particularly limited as long as a target can be heated to a predetermined temperature. Examples can include: a method for heating by irradiating a target site and/or its vicinity with, for example, a microwave, near-infrared radiation, far-infrared radiation, visible light, or electromagnetic wave; a method for heating by performing moxibustion at or near a target site; a method for heating a target site and/or its vicinity by using warm water (e.g., in a bath); a method for heating a target site and/or its vicinity by using steam (e.g. in a sauna); a method for heating by inserting into a lumen of the esophagus or rectum a probe which can generate heat; and a method for heating by inserting several electrode probes into a cancerous tissue. Because a cancer lesion is easily heated with certain precision and the heating process is relatively easy, preferred among them is a method for heating by irradiating a target site and/or its vicinity with, for example, a microwave, near-infrared radiation, far-infrared radiation, visible light, or electromagnetic wave. Among them, the electromagnetic wave can readily reach deep inside the body. Hence, more preferred is a method for heating by irradiating a target site and/or its vicinity with an electromagnetic wave. Note that an enhancer of the present invention is an enhancer for cancer thermotherapy not combined with photodynamic therapy. But, the enhancer may be combined with a method (e.g., surgical treatment, chemotherapy, immune therapy) other than the photodynamic therapy.

Preferable examples of the origin of the cells of interest described above or the organism of interest can include mammals. Preferred examples include a human, monkey, mouse, rat, hamster, guinea pig, cow, pig, horse, rabbit, sheep, goat, cat, and dog. More preferred among them may be a human.

As used in the present invention, the term "cancer" can refer to cancer and/or tumor in which an epithelial cell, etc., is malignantly transformed (e.g., malignant melanoma (melanoma), skin cancer, lung cancer, tracheal and bronchial cancer, oral epithelial cancer, esophageal cancer, gastric cancer, colonic cancer, rectal cancer, colon cancer, liver and intrahepatic bile duct cancer, renal cancer, pancreatic cancer, prostate cancer, breast cancer, uterine cancer, ovarian cancer, brain tumor); cancer and/or tumor in which a muscle and/or bone cell constituting a supporting tissue is malignantly transformed (e.g., myosarcoma, osteosarcoma, Ewing's sarcoma); and hematopoietic cancer and/or tumor (e.g., leukemia, malignant lymphoma, myeloma, Burkitt's lymphoma). Because the cancer thermotherapy is readily applicable and the subject can most benefit from an enhancing effect of the enhancer of the present invention, preferable examples of the cancer among them can include fibrosarcoma, melanoma, colon cancer, as well as cancers with intraperitoneal metastasis.

Note that examples of substantially similar aspects to the present invention can include: use of 5-aminolevulinic acids according to the present invention in the manufacture of an enhancer of the present invention; a method for using 5-aminolevulinic acids according to the present invention as an enhancer of the present invention; use of an enhancer of the present invention in cancer prophylaxis and/or treatment using cancer thermotherapy not combined with photodynamic therapy; and a method for enhancing an anticancer effect of cancer thermotherapy not combined with photodynamic therapy, comprising administering an enhancer of the present invention to a subject. Hereinabove, term contents and preferable aspects of such use and methods have been described.

The following details the present invention by referring to Examples. The present invention, however, is not limited to these Examples.

EXAMPLES

Example 1

Assay for Intracellular Reactive Oxygen Species

To investigate what kind of effect 5-aminolevulinic acids according to the present invention could exert on a level of intracellular reactive oxygen species during thermotherapy, human embryonic kidney-derived HEK293 cells and a DCF-DA fluorescent reagent (2',7'-dichlorodihydrofluorescein diacetate; $H_2DCFDA$) were used to perform an assay for measuring a level of intracellular reactive oxygen species. Note that this assay uses characteristics as follows. Cell-permeable $H_2DCFDA$ remains a non-fluorescent substance until it is oxidized in the cytoplasm of a viable cell. Once it enters the viable cell, its diacetate group is cleaved by an intracellular esterase. Then, the resulting molecule is further oxidized by reactive oxygen species to emit fluorescence. The higher the measured fluorescence level, the higher the level of intracellular reactive oxygen species. This assay was performed using the following procedure.

First, HEK293 cells were cultured at 37° C. for 24 hours in 10% fetal bovine serum (FBS)-containing Dulbecco's Modified Eagle (DME) medium. The cells were split into 8 groups. Next, the medium was replaced by an FBS-free DME medium. Then, 5-aminolevulinic acid (5-ALA) was added to each group at a final concentration of 0.5 mM, 1.0 mM, or 2.0 mM, and cultured at 37° C. for 2 hours. After that, 10% FBS was added, and the resulting HEK293 cells were incubated at 37 or 42° C. for 24 hours. In addition, 5-ALA-free HEK293 cells were likewise incubated at 37 or 42° C. for 24 hours. All the above culture processes were conducted in the dark, so that an ultraviolet light, visible light, infrared light, or radiation, etc., was never used for irradiation.

Furthermore, to each group of the HEK293 cells was added a DCF-DA fluorescent reagent (manufactured by Sigma-Aldrich Corporation) at a final concentration of 20 μM. The resulting mixture was incubated for 30 minutes. Then, fluorescence (FL1: green fluorescence) derived from the DCF-DA was measured for each group by flow cytometry (FACS-Calibur, manufactured by Becton, Dickinson and Company). Note that an excitation light emitted on a cell by a flow cytometer was used for only measurement, which does not affect cell death. The graph of FIG. 1 shows fluorescence peak values of each group. The results of FIG. 1 demonstrated that addition of 5-ALA somewhat increased a level of intracellular reactive oxygen species even at an incubation temperature of 37° C., and that the addition markedly increased a level of intracellular reactive oxygen species at an incubation temperature of 42° C. More specifically, when 0.5 mM of 5-ALA was added at an incubation temperature of 42° C., the level of intracellular reactive oxygen species was increased by 1.23 times (300/244) compared with that of the 5-ALA-free cells. When 1.0 mM of 5-ALA was added, the level of intracellular reactive oxygen species was increased by 1.34 times (326/244). When 2.0 mM of 5-ALA was added, the level of intracellular reactive oxygen species was increased by 1.42 times (346/244).

Example 2

Hyperthermia Sensitivity Test Using Flow Cytometry

To investigate what kind of effect the addition of 5-ALA could exert on hyperthermia sensitivity of cancer cells, a hyperthermia sensitivity test was performed using a flow cytometry technique as follows.

First, a human fibrosarcoma cell line HT-1080 and a colon cancer-derived cell line Caco-2 were prepared as cancer cell lines, and a human fibroblast line WI-38 and a murine fibroblast line NIH3T3 were prepared as normal cell lines. Also, prepared was a human embryonic kidney cell line HEK293 transformed so as to overgrow like cancer cells. These cells were cultured at 37° C. for 24 hours in 10% FBS-containing DME medium, and split into 8 groups. Next, the medium was replaced by an FBS-free DME medium. Then, 5-aminolevulinic acid (5-ALA) was added to each group at a final concentration of 0.5 mM, 1.0 mM, or 2.0 mM, and cultured at 37° C. for 2 hours. After that, 10% FBS was added, and the resulting cell groups were incubated at or 42° C. for 24 hours. In addition, 5-ALA-free cell groups were likewise incubated at 37 or 42° C. for 24 hours. All the above culture processes were conducted in the dark, so that an ultraviolet light, visible light, infrared light, or radiation, etc., was never used for irradiation.

Figure 2:
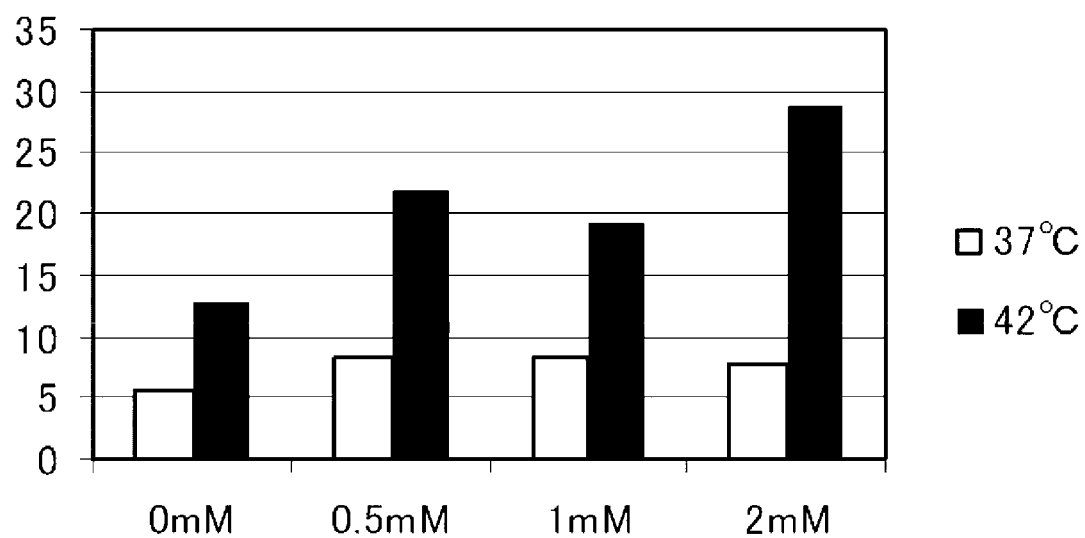
FIG. 2 illustrates the results of a hyperthermia sensitivity test using flow cytometry on a human fibrosarcoma cell line HT-1080. In the graph, the abscissa represents a 5-ALA concentration (mM), and the ordinate represents the fraction of dead cells (%).
Figure 3:
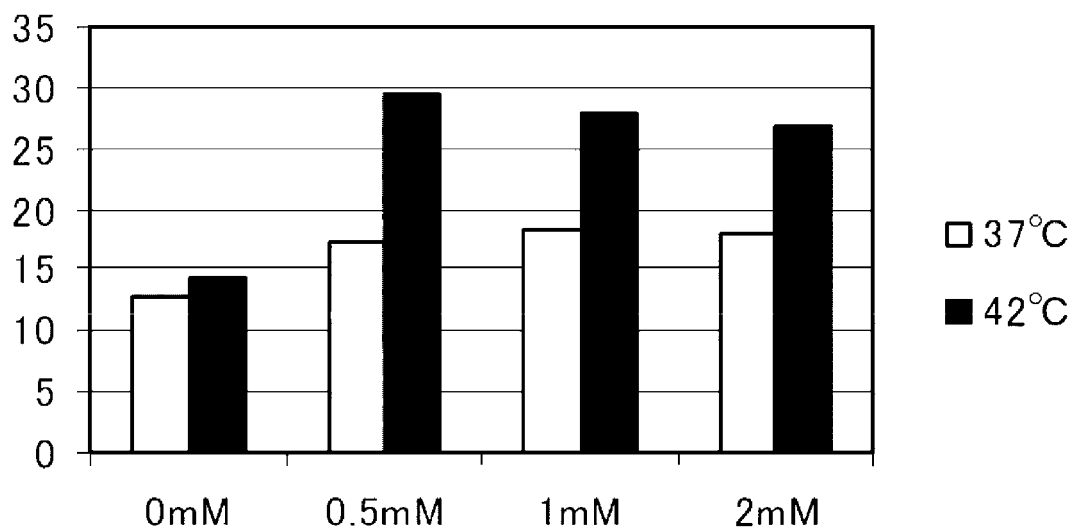
FIG. 3 illustrates the results of a hyperthermia sensitivity test using flow cytometry on a colon cancer-derived cell line Caco-2. In the graph, the abscissa represents a 5-ALA concentration (mM), and the ordinate represents the fraction of dead cells (%).
Figure 4:
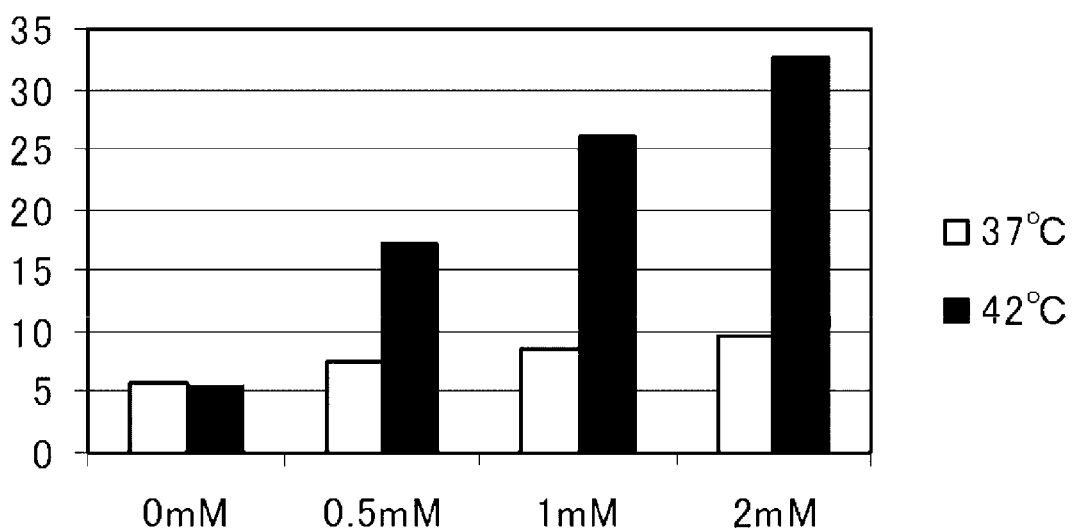
FIG. 4 illustrates the results of a hyperthermia sensitivity test using flow cytometry on a human embryonic kidney cell line HEK293 transformed so as to overgrow like cancer cells. In the graph, the abscissa represents a 5-ALA concentration (mM), and the ordinate represents the fraction of dead cells (%).
Figure 5:
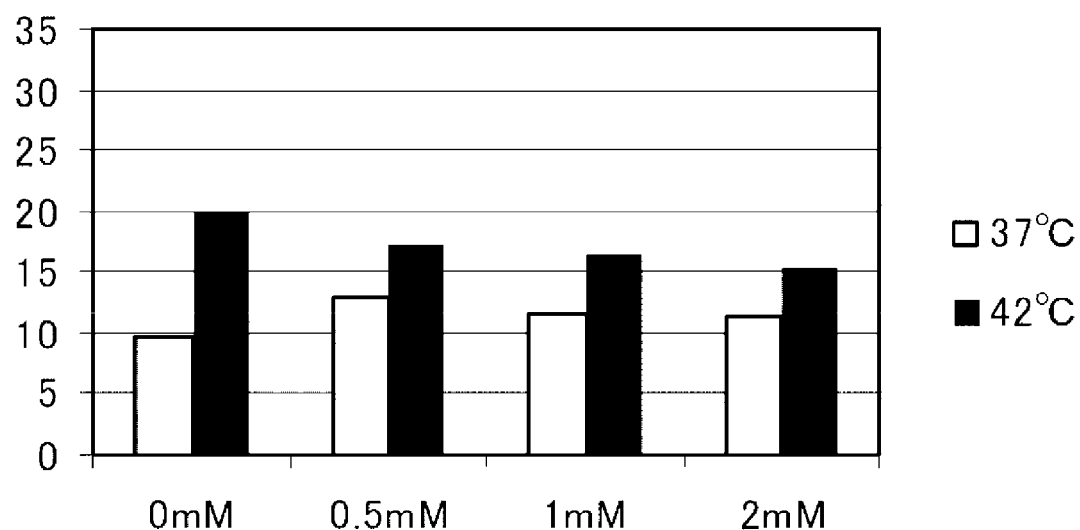
FIG. 5 illustrates the results of a hyperthermia sensitivity test using flow cytometry on a human fibroblast line WI-38. In the graph, the abscissa represents a 5-ALA concentration (mM), and the ordinate represents the fraction of dead cells (%).
Figure 6:
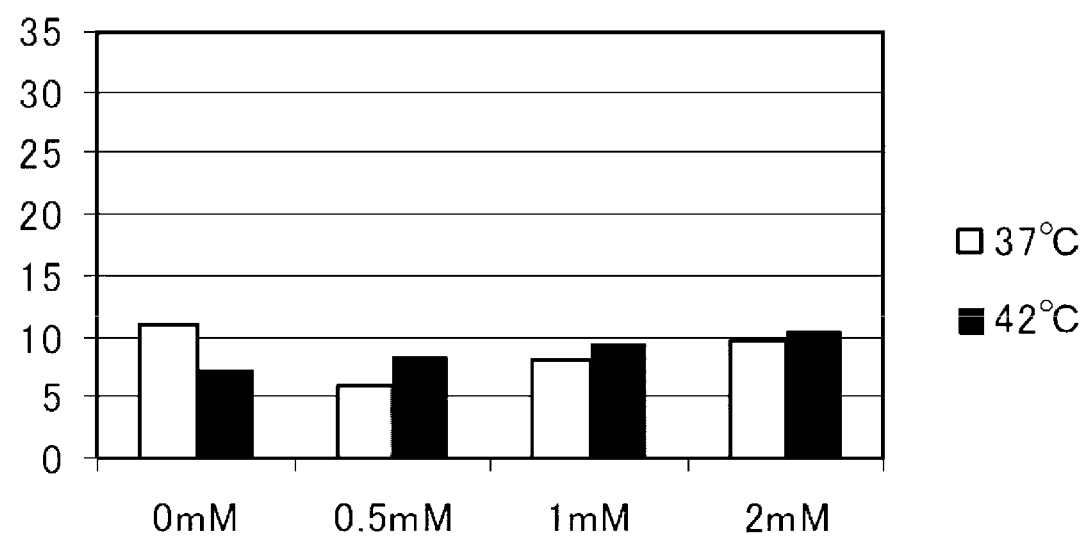
FIG. 6 illustrates the results of a hyperthermia sensitivity test using flow cytometry on a murine fibroblast line NIH3T3. In the graph, the abscissa represents a 5-ALA concentration (mM), and the ordinate represents the fraction of dead cells (%).

Next, the fraction of dead cells (%) of each group was determined using flow cytometry and a MEBCYTO-apoptosis kit, manufactured by Medical & Biological Laboratories Co., Ltd. Note that an excitation light emitted on a cell by a flow cytometer was used for only measurement, which does not affect cell death. With regard to the fraction of dead cells, a total number of cells having apoptosis and necrosis was counted, and a ratio of the total number to the number of all cells was calculated. FIG. 2 shows the results of HT-1080; FIG. 3 shows the results of Caco-2; FIG. 4 shows the results of HEK293; FIG. 5 shows the results of WI-38; and FIG. 6 shows the results of NIH3T3. It is clear from FIGS. 2 to 4 that when 5-ALA was added at an incubation temperature of 37° C., the fraction of dead cells (%) somewhat increased on cancer cell lines, HT1080 and Caco-2, and HEK293 transformed so as to overgrow like cancer cells. When these cells were incubated at a temperature of 42° C., however, the fraction of dead cells (%) was demonstrated to increase markedly. In contrast, FIGS. 5 and 6 show that 5-ALA concentration-dependent cell death was not enhanced in normal cells, WI-38 and NIH3T3, under culture conditions at 42° C. In view of the above, while an effect of enhancing cell death by 5-ALA under culture conditions at 42° C. was hardly achieved in the normal cells, the cancer cells or cancer cell-like overgrowing cells markedly exhibited the effect. Thus, when 5-ALA was combined with cancer thermotherapy, an anticancer effect (cell death-inducing effect) was remarkably enhanced in the cancer thermotherapy. Of note is little enhancement of the cell death-inducing effect in normal cells. This demonstrated that when 5-ALA is combined with cancer thermotherapy, it exerts an excellent anticancer effect on cancer cells while minimizing damage to normal cells.

The following details the results of HT-1080 in FIG. 2. When 0.5 mM of 5-ALA was added at an incubation temperature of 42° C., the fraction of dead cells (%) was increased by about 1.7 times compared with that of the 5-ALA-free cells. When 1.0 mM of 5-ALA was added, the fraction of dead cells (%) was increased by about 1.5 times. When 2.0 mM of 5-ALA was added, the fraction of dead cells (%) was increased by about 2.3 times. Also, the following details the results of Caco-2 in FIG. 3. When 0.5 mM of 5-ALA was added at an incubation temperature of 42° C., the fraction of dead cells (%) was increased by about 2.1 times compared with that of the 5-ALA-free cells. When 1.0 mM of 5-ALA was added, the fraction of dead cells (%) was increased by about 2.0 times. When 2.0 mM of 5-ALA was added, the fraction of dead cells (%) was increased by about 1.9 times. Furthermore, the following details the results of HEK293 in FIG. 4. When 0.5 mM of 5-ALA was added at an incubation temperature of 42° C., the fraction of dead cells (%) was increased by about 3.2 times compared with that of the 5-ALA-free cells. When 1.0 mM of 5-ALA was added, the fraction of dead cells (%) was increased by about 4.8 times. When 2.0 mM of 5-ALA was added, the fraction of dead cells (%) was increased by about 6.0 times.

Example 3

Hyperthermia Sensitivity Test Using Trypan Blue Reagent

A colon cancer-derived cell line Caco-2, a human hepatoma-derived cell line HepG2, a human gastric cancer-derived cell line KatoIII, and a human cervical cancer-derived cell line HeLa were used as cancer cell lines. A human embryonic kidney cell line HEK293 was used as cells transformed so as to overgrow like cancer cells. A human normal diploid fibroblast line WI-38, a murine fibroblast-like cell line NIH3T3, and a human embryonic lung-derived normal fibroblast MRCS were used as normal cells. Each of these cells was cultured at 37 or 42° C. for 24 hours in a DME medium containing 10% FBS and 5-ALA at a concentration of 0, 0.5, 1, or 2 mM, and treated with trypsin for cell harvest. Then, equal volumes of the harvested cell-containing solution and a trypan blue reagent were mixed, and the number of the cells was counted with a hemocytometer to calculate the fraction of dead cells (cells stained with trypan blue) (%; percent cell death).

Figure 8:
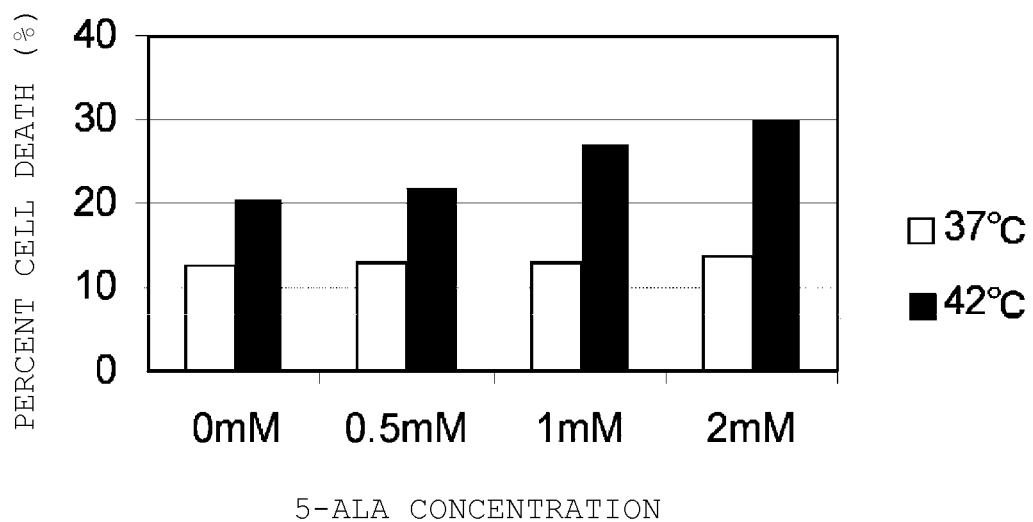
FIG. 8 illustrates the results of a hyperthermia sensitivity test using a trypan blue reagent and a human hepatoma-derived cell line HepG2. In the graph, the abscissa represents a 5-ALA concentration (mM), and the ordinate represents the fraction of dead cells (%).
Figure 9:
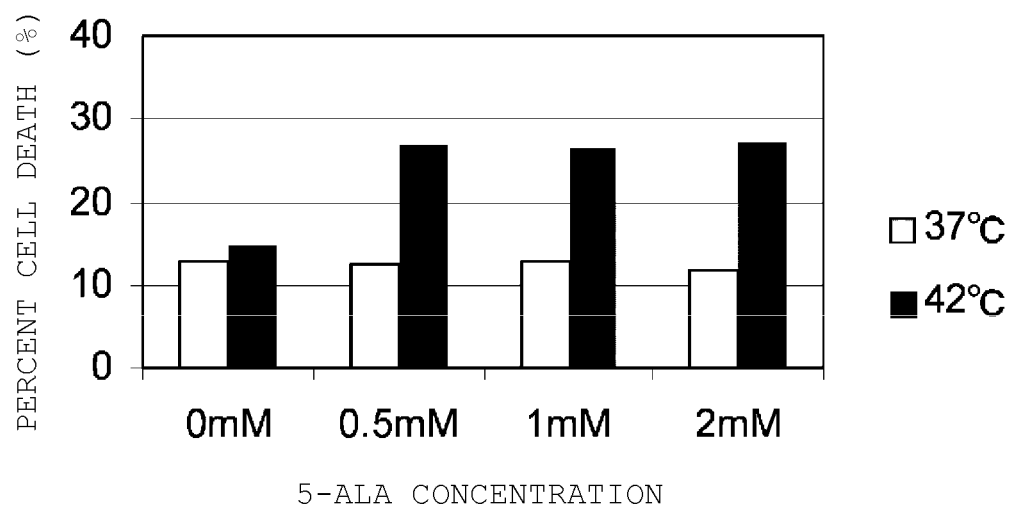
FIG. 9 illustrates the results of a hyperthermia sensitivity test using a trypan blue reagent and a human gastric cancer-derived cell line KatoIII. In the graph, the abscissa represents a 5-ALA concentration (mM), and the ordinate represents the fraction of dead cells (%).
Figure 10:
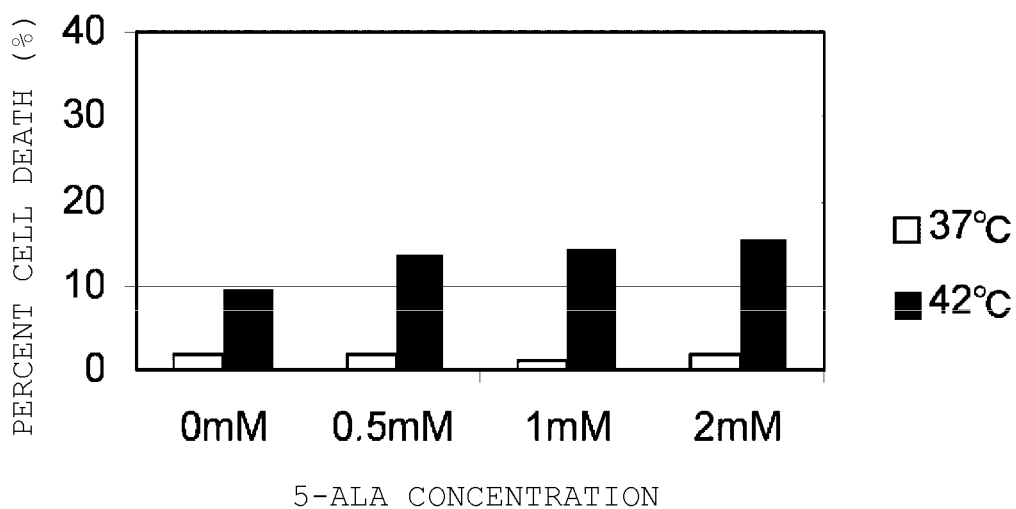
FIG. 10 illustrates the results of a hyperthermia sensitivity test using a trypan blue reagent and a human cervical cancer-derived cell line HeLa. In the graph, the abscissa represents a 5-ALA concentration (mM), and the ordinate represents the fraction of dead cells (%).
Figure 11:
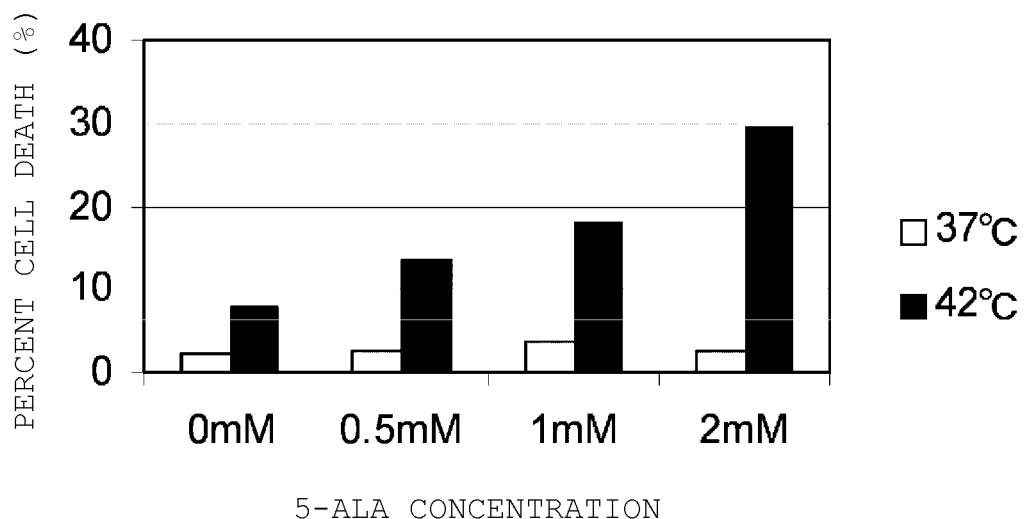
FIG. 11 illustrates the results of a hyperthermia sensitivity test using a trypan blue reagent and a human embryonic kidney cell line HEK293 transformed so as to overgrow like cancer cells. In the graph, the abscissa represents a 5-ALA concentration (mM), and the ordinate represents the fraction of dead cells (%).
Figure 12:
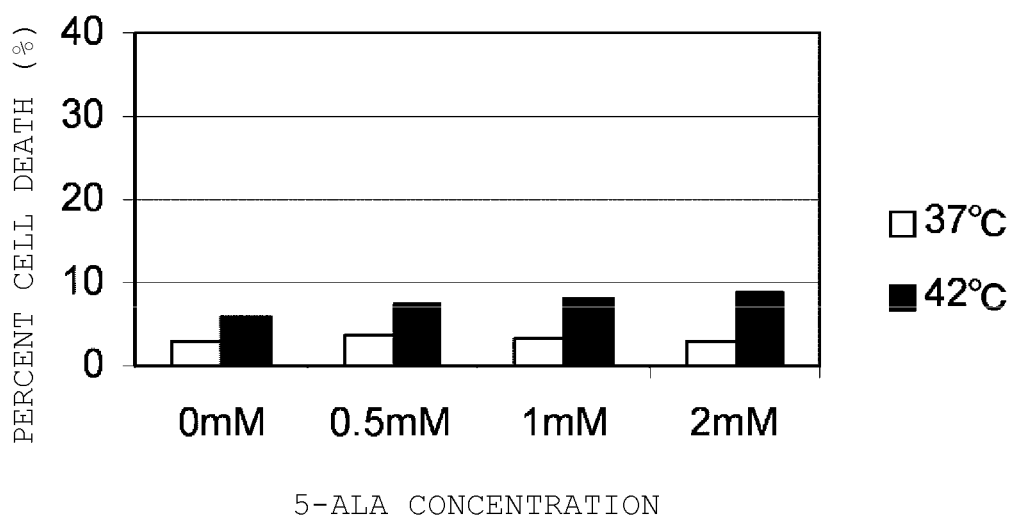
FIG. 12 illustrates the results of a hyperthermia sensitivity test using a trypan blue reagent and a human normal diploid fibroblast line WI-38. In the graph, the abscissa represents a 5-ALA concentration (mM), and the ordinate represents the fraction of dead cells (%).
Figure 13:
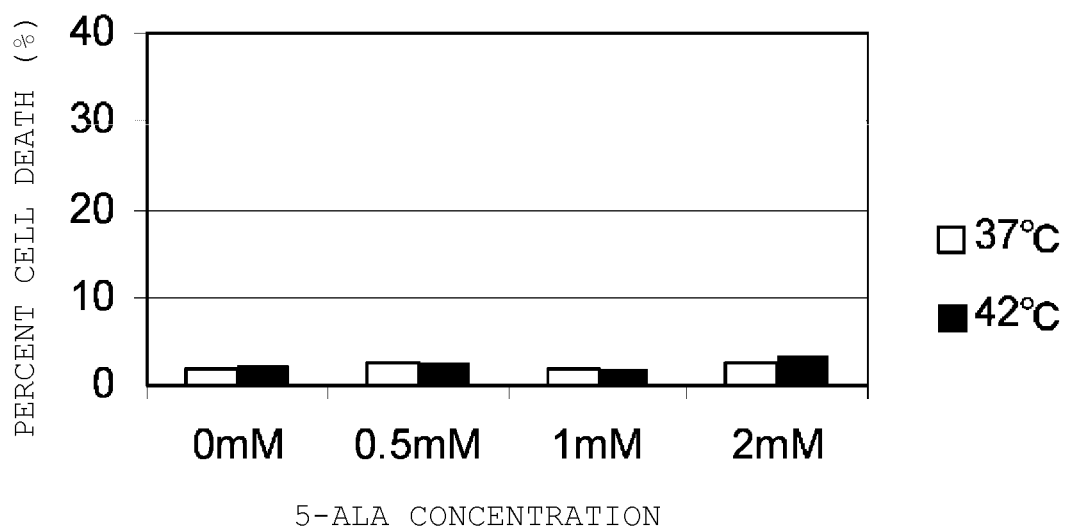
FIG. 13 illustrates the results of a hyperthermia sensitivity test using a trypan blue reagent and a murine fibroblast-like cell line NIH3T3. In the graph, the abscissa represents a 5-ALA concentration (mM), and the ordinate represents the fraction of dead cells (%).
Figure 14:
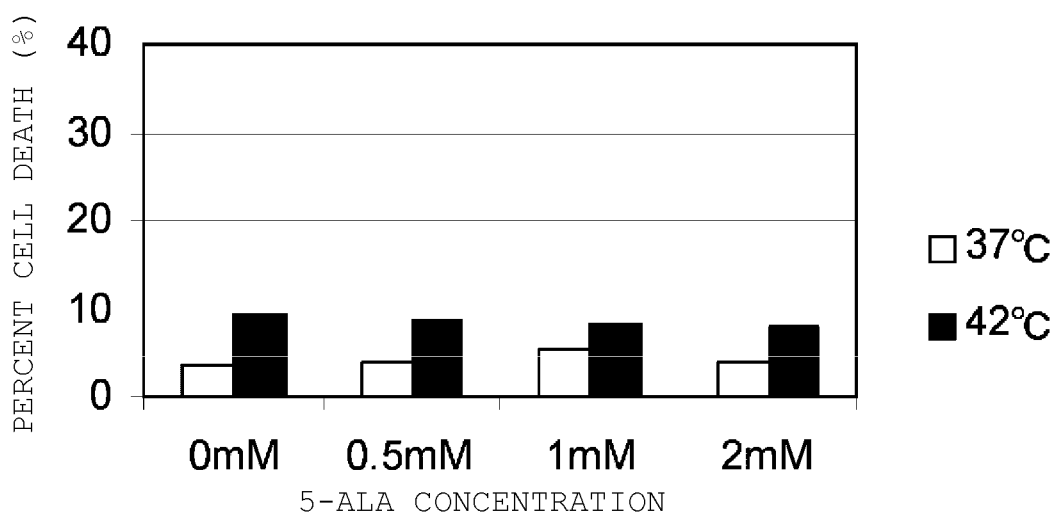
FIG. 14 illustrates the results of a hyperthermia sensitivity test using a trypan blue reagent and human embryonic lung-derived normal fibroblasts MRCS. In the graph, the abscissa represents a 5-ALA concentration (mM), and the ordinate represents the fraction of dead cells (%).

The results demonstrated that when each concentration of 5-ALA was added and incubated at 37° C., the fraction of dead cells did not increase in each of the cancer cells (i.e., Caco-2 (see FIG. 7), HepG2 (See FIG. 8), KatoIII (see FIG. 9), and HeLa (see FIG. 10)) and the human embryonic kidney cell line HEK293 (See FIG. 11) which overgrows like cancer cells. When these cells were incubated at 42° C., however, the fraction of dead cells markedly increased depending on the 5-ALA concentration. It was observed that the transformed human embryonic kidney cell line HEK293, in particular, had a remarkable 5-ALA-concentration dependency. In contrast, when each of the normal cells (i.e., WI-38 (see FIG. 12), NIH3T3 (see FIG. 13), and MRCS (see FIG. 14)) was incubated at 42° C., no increase in the fraction of dead cells depending on the 5-ALA concentration was detected. These results demonstrated that when combined with cancer thermotherapy, 5-ALA enhanced an anticancer effect on cancer cells while minimizing damage to normal cells. The above results were similar to those of the hyperthermia sensitivity test using flow cytometry in the above Example 2.

Figure 7:
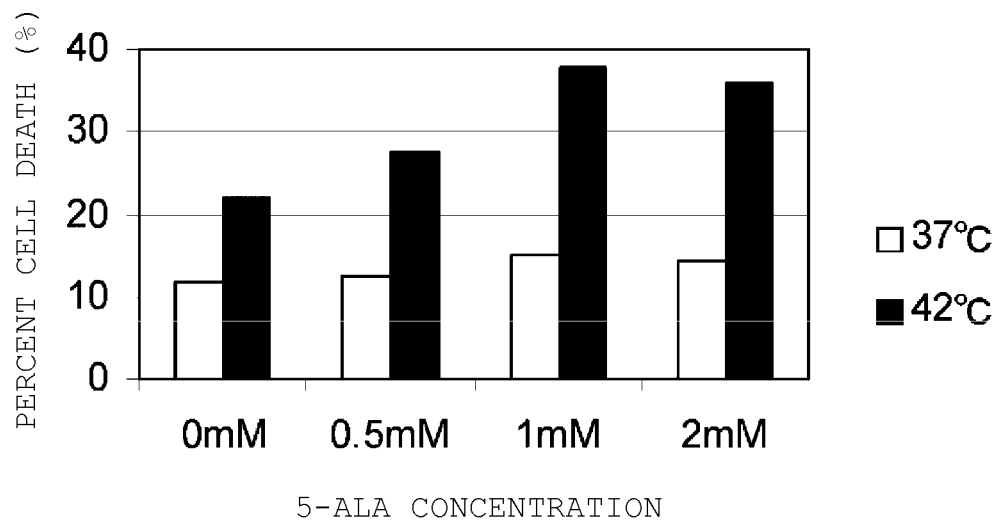
FIG. 7 illustrates the results of a hyperthermia sensitivity test using a trypan blue reagent and a colon cancer-derived cell line Caco-2. In the graph, the abscissa represents a 5-ALA concentration (mM), and the ordinate represents the fraction of dead cells (%; percent cell death).

Also, the following details the results of Caco-2 in FIG. 7. When 0.5 mM of 5-ALA was added at an incubation temperature of 42° C., the fraction of dead cells (%) increased by about 1.2 times compared with that of the 5-ALA-free cells. When 1.0 mM of 5-ALA was added, the fraction of dead cells (%) increased by about 1.7 times. When 2.0 mM of 5-ALA was added, the fraction of dead cells (%) increased by about 1.6 times. In addition, the following details the results of HepG2 in FIG. 8. When 0.5 mM of 5-ALA was added at an incubation temperature of 42° C., the fraction of dead cells (%) increased by about 1.1 times compared with that of the 5-ALA-free cells. When 1.0 mM of 5-ALA was added, the fraction of dead cells (%) increased by about 1.35 times. When 2.0 mM of 5-ALA was added, the fraction of dead cells (%) increased by about 1.5 times. Further, the following details the results of KatoIII in FIG. 9. When 0.5 mM of 5-ALA was added at an incubation temperature of 42° C., the fraction of dead cells (%) increased by about 1.8 times compared with that of the 5-ALA-free cells. When 1.0 mM of 5-ALA was added, the fraction of dead cells (%) increased by about 1.8 times. When 2.0 mM of 5-ALA was added, the fraction of dead cells (%) increased by about 1.8 times. Furthermore, the following details the results of HeLa in FIG. 10. When 0.5 mM of 5-ALA was added at an incubation temperature of 42° C., the fraction of dead cells (%) increased by about 1.4 times compared with that of the 5-ALA-free cells. When 1.0 mM of 5-ALA was added, the fraction of dead cells (%) increased by about 1.5 times. When 2.0 mM of 5-ALA was added, the fraction of dead cells (%) increased by about 1.6 times. Moreover, the following details the results of HEK293 in FIG. 11. When 0.5 mM of 5-ALA was added at an incubation temperature of 42° C., the fraction of dead cells (%) increased by about 1.6 times compared with that of the 5-ALA-free cells. When 1.0 mM of 5-ALA was added, the fraction of dead cells (%) increased by about 2.0 times. When 2.0 mM of 5-ALA was added, the fraction of dead cells (%) increased by about 3.5 times.

Example 4

Measuring Intracellular PpIX Concentration by HPLC

Additional investigation was conducted using a transformed human embryonic kidney cell line HEK293 which exhibited a remarkable effect of 5-ALA when combined with heat treatment in the above Example 3. In addition, a normal cell line WI-38, which did not exhibit an effect of 5-ALA when combined with heat treatment, was used as a control. These two types of cells were cultured at 37 or 42° C. for 24 hours in a DME medium containing 10% FBS and 5-ALA at a concentration of 0, 0.5, 1, or 2 mM. Next, the cells were harvested using trypsin treatment. Then, the number of cells contained in a measurement sample was adjusted using a hemocytometer at $1 \times 10^4$. After that, the cells were lysed with NaOH, and treated with a DMF solution (i.e., a mixture of N,N-dimethylformamide:2-propanol=100:1). The resulting cell lysate was centrifuged at 13,000 rpm and 4° C. for 10 minutes to collect a supernatant. Subsequently, the supernatant was reacted at room temperature for 24 hours. Finally, the resulting supernatant was used as a measurement sample, and was subjected to a PpIX concentration measurement using HPLC.

Figure 15:
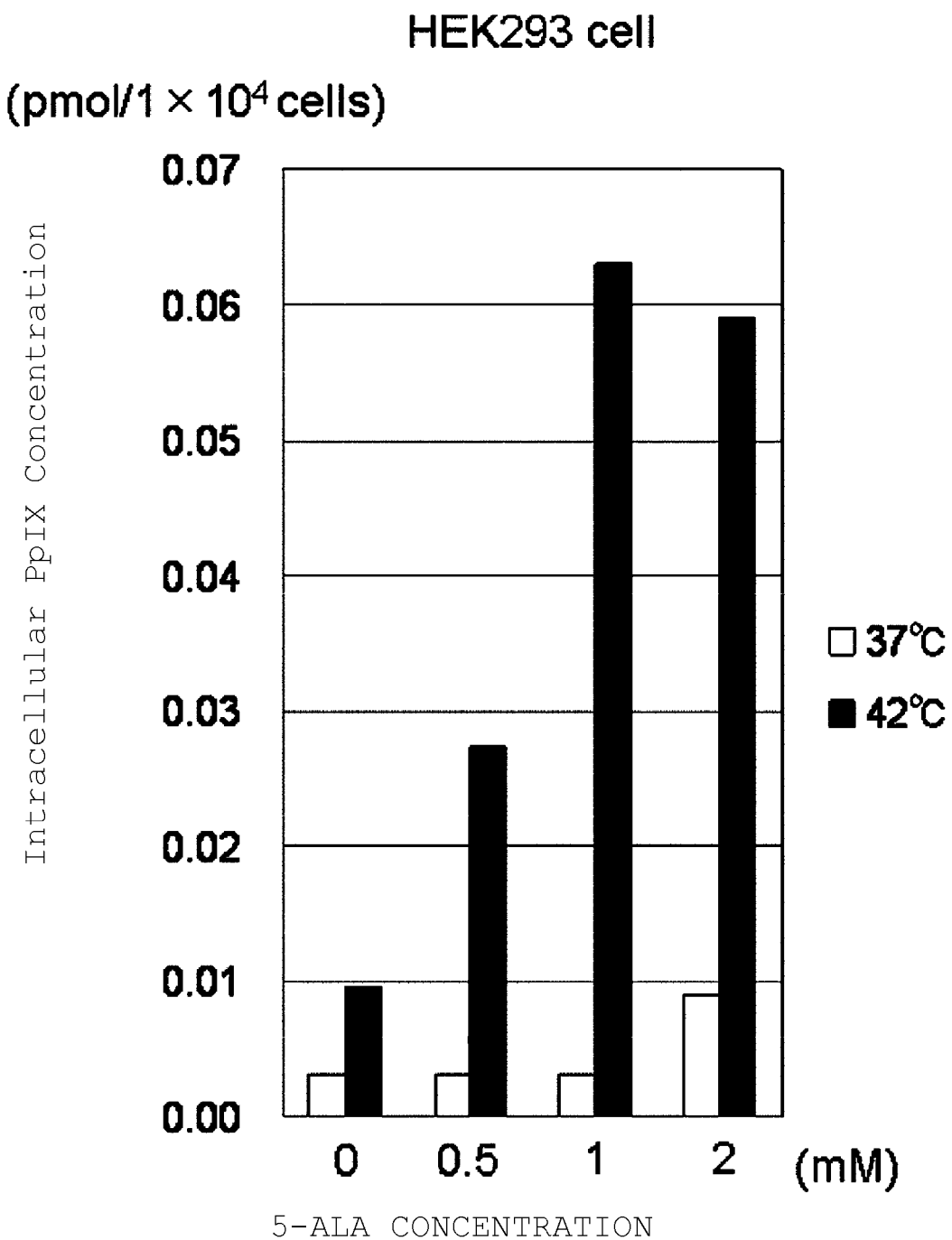
FIG. 15 illustrates the results of measuring an intracellular PpIX concentration in the HEK293 cell line by HPLC. In the graph, the abscissa represents a 5-ALA concentration (mM), and the ordinate represents an intracellular PpIX concentration.

FIG. 15 illustrates the results of measuring an intracellular PpIX concentration in the above HEK293 cell line by HPLC. A PpIX concentration in the HEK293 cell line was found to be increased depending on the 5-ALA concentration under culture conditions at 42° C. This result suggests that an enhancing effect of 5-ALA on thermotherapy illustrated in the above Example 3 should be exerted depending on 5-ALA. Also, the following details the results of HEK293 in FIG. 15. When 0.5 mM of 5-ALA was added at an incubation temperature of 42° C., an intracellular PpIX concentration was increased by about 2.75 times compared with that of the 5-ALA-free cells. When 1.0 mM of 5-ALA was added, the intracellular PpIX concentration was increased by about 6.3 times. When 2.0 mM of 5-ALA was added, the intracellular PpIX concentration was increased by about 5.9 times. In contrast, although the results are not shown in any figure, a normal cell line WI-38 had a detection limit or less of the intracellular PpIX concentration regardless of the 5-ALA concentration added in any of the measurement samples tested in this experiment. These results support that the combination of 5-ALA and heat treatment does not damage normal cells as demonstrated in the above Example 3.

INDUSTRIAL APPLICABILITY

The present invention is suitably available in the field of cancer treatment and, more specifically, the field of enhancer for cancer thermotherapy not combined with photodynamic therapy.

The invention claimed is:

1. A method for enhancing cancer thermotherapy, wherein said thermotherapy is not administered together with photodynamic therapy, comprising the following steps (A) and (B):

(A) a step of administering 5-aminolevulinic acids represented by formula (1):

$$R^2R^1NCH_2COCH_2CH_2COR^3 \qquad (1)$$

wherein $R^1$ and $R^2$ each independently represent a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group, or a salt thereof to a patient suffering from cancer; and (B) a step of heating a cancer lesion of the patient to a range from 41 to 44° C.

2. The method according to claim 1, wherein heating is performed after waiting for 3 to 7 hours after administering 5-aminolevulinic acids or a salt thereof to the patient.

3. The method according to claim 1, wherein heating is performed for 15 minutes to 3 hours.

4. The method according to claim 1, wherein 5-aminolevulinic acids or a salt thereof are not encapsulated inside a lipid membrane or in an internal aqueous phase thereof.

5. The method according to claim 1, wherein the patient suffers from colon cancer, gastric cancer, cervical cancer, and/or hepatoma.

* * * * *